United States Patent

Gracey et al.

[11] Patent Number: 6,103,801
[45] Date of Patent: Aug. 15, 2000

[54] 2-SUBSTITUTED SUCCINATE ESTERS

[75] Inventors: Benjamin Patrick Gracey, Hull; Christopher Hallett, Watford, both of United Kingdom

[73] Assignee: BP Chemicals Limited, London, United Kingdom

[21] Appl. No.: 09/019,353

[22] Filed: Feb. 5, 1998

Related U.S. Application Data

[63] Continuation of application No. PCT/GB97/01742, Jun. 27, 1997.

[30]     Foreign Application Priority Data

Jun. 28, 1996 [GB] United Kingdom ............ 9613679
Nov. 27, 1996 [GB] United Kingdom ............ 9624680

[51] Int. Cl.$^7$ .................... C08K 5/12; C07C 67/08; C07C 69/708
[52] U.S. Cl. ................ 524/308; 560/198; 560/201; 560/181; 560/182; 560/183; 568/828; 568/909.5
[58] Field of Search ............... 560/181, 182, 560/183, 198, 201; 524/308; 568/909.5, 828

[56]     References Cited

U.S. PATENT DOCUMENTS

| | | |
|---|---|---|
| 2,221,663 | 11/1940 | Rothrock ................... 560/198 |
| 2,346,612 | 11/1944 | Rothrock ................... 560/198 |
| 2,404,313 | 7/1946 | Rodman . |
| 2,571,212 | 10/1951 | Croxall et al. ............ 260/484 |
| 3,172,904 | 3/1965 | Rehfuss . |
| 3,303,241 | 2/1967 | Moorshead ............... 260/884 |
| 3,499,042 | 3/1970 | Smutny ................... 260/614 |
| 5,118,885 | 6/1992 | Tokitoh et al. .......... 568/909.5 |

FOREIGN PATENT DOCUMENTS

| | | |
|---|---|---|
| 552715 | 4/1943 | United Kingdom . |
| WO 97/02229 | 1/1997 | WIPO . |
| WO 97/02230 | 1/1997 | WIPO . |

*Primary Examiner*—Veronica P. Hoke
*Attorney, Agent, or Firm*—Fay, Sharpe, Fagan, Minnich & McKee, LLP

[57]     ABSTRACT

This invention relates to a process for producing 2-substituted succinate esters of formula (I) by reacting (a) a dicarboxylic compound with a first alcohol R'O[CH'.CH$_2$O]$_x$H where x is 0 or an integer from 1–6 in the presence of a catalyst to form a hydrocarbyl ester or, when x=1–6, a hydrocarbyloxy alkylene ester of maleic and/or fumaric acid and (b) the ester from step (a) with an alkaline earth metal alkoxide in the presence of a second alcohol R.OH to form the 2-substituted succinate ester of formula (I). The esters and paint formulations based thereon are also claimed.

12 Claims, No Drawings

2-SUBSTITUTED SUCCINATE ESTERS

This application is a continuation of co-pending International Application No. PCT/GB97/01742 filed on Jun. 27, 1997.

This invention relates to a process for producing 2-substituted succinate esters with low colour and use of said ether esters as diluents in paint and polymer formulations, One of the processes used hitherto to produce 2-substituted succinate esters is the combined transesterification and Michael addition reaction of an alcohol or a monoether of a polyoxyalkylene glycol as described in GB-A-552715 in which ether esters of hydroxysuccinic acid and unsaturated alcohols are prepared by reacting in a single step under anhydrous conditions an alkyl ester of maleic acid with an unsaturated alcohol in the presence of a magnesium alkoxide catalyst. However, this method when repeated for instance with an octadienol/di methyl maleate system using magnesium methoxide as a catalyst gives products which have a deep red colour. It may be possible to overcome this colour problem in the products described in this prior art by distillation. However, such a method is unlikely to be practicable with the synthesis of esters contemplated in the present invention since they are all meant to have relatively low volatility and hence are not amenable to purification by distillation.

It has now been found that 2-substituted succinate esters some of which are novel, can be produced in commercially viable yields and purity by using a two-stage process.

Accordingly, the present invention relates to a process for producing 2-substituted succinate esters of the formula (1) said process comprising reacting
a. a dicarboxylic compound selected from the group consisting of maleic acid, maleic anhydride, fumaric acid and the dialkyl ester of maleic or fumaric acid with an alcohol R'O[CH$_2$O], H where x is 0 or an integer from 1–6 in the presence of a catalyst to form a hydrocarbyl ester or, when x=1–6, a hydrocarbyloxy alkylene ester of maleic and/or fumaric acid and
b. the ester front step (a) with an alkaline earth metal alkoxide in the presence of a further amount of the alcohol to form the 2-substituted succinate ester of formula (1)

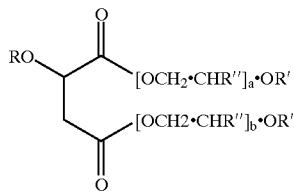

(I)

in which
R and R' are each an unsaturated hydrocarbyl or allyically unsaturated hydrocarbyloxy alkylene group having, at least 5 carbon atoms,
R" is H or an alkyl or an alkylene group having 1 to 2 carbon atoms and, each of a and b is same or different and has a value of 0 or is an integer from 1–6.

By the expression "alkylene" as used herein and throughout the specification is meant a divalent hydrocarbyl group such as eg a —CH$_2$(CHR")—CH$_2$-group wherein, **=0 or an integer and R" has the same notation as above.

R' is derived from the reactant alcohol R'O[CHR".CH$_2$O]$_x$H where x is 0 or an integer from 1–6 which is used for making the succinate ester and can be an allylic hydrocarbyl or an allylic hydrocarbyloxy alkylene group. Thus, the reactant alcohol is an allylic alcohol and includes inter alia 2-ethyl-hex-2-en-1-ol;- 2-octen-1-1-octen--3-ol; 2,7-octadienol, 2-ethyl allyl alcohol; hept-3-en-2-ol; 4-methyl pent-3-en-2-ol; 4-t-butoxy but-2-en-1-ol (also called 1,4-but-2-ene diol mono-tertiary butyl ether); 4-n-butoxy but-2-en-1-ol (also called 1,4-but-2-ene diol mono-n-butyl ether): cinnamyl alcohol; and isophorol.

The reactant alcohol, R'O[CHR".CH$_2$O]$_x$H where x is 0 or an integer from 1–6 can be prepared in several ways known to those skilled in the art. For instance, this reactant alcohol, eg an allylic alcohol, can be produced by the reduction of the corresponding α, β-unsaturated aldehyde eg by hydrogenation, which will generate a mixture of the allylic alcohol and its saturated analogue. Some other allylic alcohols may be produced from conjugated dienes via the well known addition reactions. Furthermore, other allylic alcohols may be produced by by hydrolysis of the ester to a mixture of isomeric allylic alcohols. This litter reaction may, like some of the other reactions mentioned above, result in & mixture of products which includes inter alia the desired allylic alcohol, isomers thereof and saturated analogues thereof. The mixtures of allylic alcohol with the saturated analogue thereof and/or the isomers thereof can be then used as such or, after further purification to isolate the desired allylic alcohol, to prepare the esters represented by formula (I) above.

Where the reactant alcohol is itself an allylic unsaturated hydroxy ether. ie x 1.6, this may be derived by alkoxylation of an alcohol. eg allylic ether alcohol, suitably in the presence of a catalyst to form the hydroxy ether. Where a catalyst is used it should be such that it does not cause rearrangement of the allylic function and hence, amphoteric, basic or acidic catalysts may be used. The catalyst can be heterogeneous or homogeneous. The alkoxylation step is suitably carried out in the presence of a base catalyst. Examples of base catalysts that may be used include alkali metal hydroxides such as sodium or potassium hydroxide and other metal salts such as potassium acetate.

The alkoxylation reaction to form the hydroxy ether of the allylic alcohol can be carried out using one or more of the epoxides which include inter alia ethylene oxide propylene oxide, butene oxide and butadiene mono-oxide. The amount of epoxide used for this step) would depend upon the number of alkoxy groups desired in the hydroxy ether. The amount of epoxide used is suitably in the range from 0.1 to 20 moles, preferably from 1 to 5 moles based on the allylic alcohol reactant.

The alkoxylation reaction is suitably carried out at a temperature in the range from 50 to 180° C., preferably from 60 to 140° C. The reaction pressure for this step is suitably autogenous but is preferably front 100 to 700 KPa.

The hydroxy ether formed in this step) is suitably separated from the reaction mixture by neturalisation using, eg magnesium silicate, then filtered to remove the neutralising agent and the salt of neutralisation so formed to leave behind filtrate comprising the desired hydroxy ether.

The hydroxy ether so produced can be used either as such without purification, or, optionally, after purification (eg by distillation) for the esterification stage.

Thus, the 2-succinate esters of formula (1) are prepared by reacting in the first stage (a) the reactant alcohol wall maleic acid or anhydride and/or fumaric acid or esters thereof in the presence of a catalyst. The catalyst used in this step can be zinc acetate, dibutyl tin oxide, stannous oxalate, para-toluene sulphonic acid or phosphoric acid. This reaction is suitably carried out at a temperature below 150° C. preferably from 100–130° C. The completion of the reaction is ascertained by GC analysis using a CP-SILS 50 m capillary column and a flame ionisation detector. Upon completion of the reaction the unreacted materials are stripped out by steam stripping or by azeotropic distillation eg using an azeotroping agent such as eg cyclohexane. The catalyst may then be neutralised or removed as appropriate, the solids filtered and the ester in the filtrate recovered.

The ester product from this step (a) is then further reacted in a step (b) with a further amount of the reactant alcohol in the presence of an alkaline earth metal alkoxide catalyst. The function of this step (b) is to enhance the amount of the desired 2-succinate ester in the product from step (a) at the expense of the maleates and fumarates in said product. The alkaline earth metal alkoxide may be derived from the .second reactant alcohol or from another alcohol. The alkaline earth metal alkoxide is preferably magnesium alkoxide. The amount of alkaline earth metal alkoxide used must be sufficient to compensate for loss of catalyst due to its reaction with any residual acids or water present in the products from stage (a) of the reaction or the reactant alcohol, The reaction with the alkaline earth metal alkoxide is suitably carried out at a temperature below 120° C. suitably in the range from 40 to 50° C. and step (b) is suitably carried out at atmospheric, subatmospheric or superatmosphesic p1pressures. The pressures used are preferably in the range from atmospheric to 50 Kpa, more preferably from atmospheric to 5 KPa. This division of the reaction into two stages allows the use of relatively milder condition than has hitherto been possible and as a consequence affords an improved product which is less coloured.

The esters formed by this process may be a mixture of the desired esters of formula (1) and the corresponding unsaturated analogues comprising the maleic acid or fumaric acid esters. Thus, for example, reaction of 2-ethyl hexenol with maleic acid or anhydride followed by reaction of the product with magnesium alkoxide of2-ethylhexenol as catalyst would give rise to a product which primarily comprises 2-(2-ethyl hexenoyl)-di[2-(2-ethyl hexenyl)) succinate. Similarly, when octadienoxy ethanol is reacted with maleic acid or anhydride, followed by the reaction of this product with the magnesium alkoxide of octadienoxy ethanol as octadienoxy) ethoxy] succinate. Both of these are novel esters not reported hitherto. Similarly, when 2,7-octadienol is reacted with dimethyl maleate, followed by reaction or the resultant product with further aliquots of the reactant alcohol in the presence of magnesium alkoxide catalyst, the product obtained is 2-octadienoxy di-octadienyl succinate.

A feature of the two-stage process of the present invention is that it uses relatively milder conditions than a conventional Michael addition reaction, For instance, no reflux conditions need be used during this step. Furthermore, the present process enables the proportion of the 2-substituted succinate ester in the reaction product to be enhanced considerably without leading to undesirable polymer formation or increasing the colouration of the ester product. Moreover, the present process gives better yields of the desired 2-substituted succinate ester due to the milder conditions employed.

The esters of the present invention have low volatility and relatively low viscosity suitably below 1500 mPa.s, thereby rendering them a suitable solvent component for curable paint and varnish formulations. These ether esters are especially suitable as the so called "reactive diluents" for paint formulations and in particular those containing alkyl resins. Reactive diluents are usually compounds or fixtures of compounds of relatively low viscosity, a relatively high boiling point (or low saturated vapour pressure) which act as solvents during the formulation and processing of the coating. An advantage of reactive diluents is that such diluents fail copolymerise with components of the alkyl resin. Hence reactive diluents may be used Lo replace part or all of the traditional solvents normally used in such formulations thereby reducing losses of the solvent to atmosphere on drying of the coating. Use of reactive diluents comprising esters of polyhydric alcohols which have been partially etherified with ally alcohol are described in EP-A-0 253 474.

Alkyd resins are well known components of decorative paints (see, for example, "The Technology of Paints, Varnishes and Lacquers" by C R Martens(Ed.). published by Robert Krieger Publishing (1974) and can be prepared from polybasic acids or anhydrides, polyhydric alcohols and fatty acids or oils. U.S. Pat. No. 3,819,720 describes methods of preparing such alkyd formulations. Alkyd coating compositions usually contain large amounts of solvents (eg of solvents (eg mineral spirits and aromatic hydrocarbons).

The compositions of the present invention are highly suitable for use as reactive diluents. The relative ratios of reactive diluent to the alkyd resin in a formulation can be derived from the ranges quoted in published EP-A-0 305 006. In an example in which the reactive diluent replaces all of the traditional solvent, the ratio of reactive diluent to alkyd resin is suitably in the range from 1–50: 99–50 parts by weight, eg 5–50: 95–50, preferably from 5–25: 95–75 and more preferably from 5–15 95–85 parts by weight. On the other hand, where used in a conventional paint formulation, such a diluent can replace all or part of a traditional solvent such as white spirit. The formulations may contain further components such as catalyst, drier, antiskinning agent, pigments, pigment stablisers, rheology controllers (eg. for sag control). UV and oxidation stabilisers, flow additives, microgels (e.g. to enhance hardness) and other additives. The formulations may also need to include water scavengers such as trialkyl orthoformates, molecular sieves or zeolites where the reactive diluent used is susceptible to hydrolysis such as eg some of the ether ester derivatives. Furthermore, where such water scavengers are used it may be necessary to use them in combination with compatible pigment stabilizers. Where a drier (siccative) is used this may further contribute towards the solvent content of the formulation.

For formulations comprising an oxidatively curing alkyd resin and a siccative/drier such as cobalt complexes, impurities which can have a co-ordination affinity for the siccative drier such as cobalt complexes can affect adversely the drying speed and stability of the paint. Examples of such impurities include maleic acid and triethyl amine. In particular it has been found desirable to minimise the acidity of the ester mixture used as reactive diluent in such formulations to a value of <7000 ppm, preferably 3000 ppm, more preferably <1000 ppm w/w of KOH.

It has also been found that when a mixture of esters, ie the succinates fumarates and maleates, is used as a reactive diluent in such formulations comprising an oxidatively curing alkyd resins, the properties/performance of the diluent call be varied by changing the relative proportions or the three esters present ill Such a diluent. For example, mixtures with a relatively lower amount of maleates exhibit better hardness and drying properties compared with those having relatively higher amounts of such maleates. Moreover, it has also been observed that formulations comprising these esters display a decreased tendency towards wrinkling. This renders them particularly suitable when using formulations comprising high solid systems/one-coat paints have to be applied to generate a greater thickness of the relevant coating without impairing the ability of such thicker layers to harden through.

For some uses it is preferable that the free alcohol content of the diluent is minimised in order to facilitate drying of the formulations A feature of the: present invention is that other esters of formula (l) when used as reactive diluents in paint or coating formulations, especially those comprising alkyd resins, enhance the performance of these formulations- In particular, where a mixture of products comprising ether esters of the present invention derived by reacting an allylic alcohol or a hydroxy ether thereof with maleic, acid/anhydride or fumaric acid is used as reactive diluent, they enhance their performance when compared with that of the unsaturated esters when used alone.

A further aspect of the present invention is that such esters when used in a relatively pure state do not cause any haze in the formulation, Where there is likely to be a risk of such haze formation, eg due to the presence of impurities such as eg resins or polymers formed during the synthesis of the esters used or during storage is of such formulations, it is beneficial to use inhibitors such as eg butylated hydroxytoluene (2,6-butoxy-4-methyl phenol) or 2,4.6-tert-butyl phenol. Such inhibitors not only have the advantage of preventing haze formation but also render the formulations safer to handle by inhibition of other unwanted reactions in the formulation such as eg peroxidation.

Uses of the molecules of this invention include the partial or total replacement of traditional hydrocarbon-based solvents in solvent-borne alkyd paints used for primer undercoat and topcoat decorative applications as well as in industrial applications such as alkyd primers and UV-cure.

The molecules of this invention are also suitable for use as co-monomers, for example in vinyl acetate-based polymers used in emulsion paints. In this case, the molecules of this invention impart a temporary plasticisation to the paint film, before air-curing to a hard finish. They can, therefore, facilitate the partial or total replacement of coalescent solvents, In addition, the molecules could be used in water-based paints based on acrylic and alkyd resins, in addition to, or instead of, coalescent solvents, The present invention is further illustrated with reference to the following Examples.

EXAMPLE 1: General Method: Reaction of an allylic ether-alcohol with a maleate

The following apparatus was assembled:
A five-liter flanged flask with an insert pipe for a nitrogen sparge, a thermowell for thermocouple, and a Dean and Stork apparatus with double-walled condenser. The flask was heated with an electric heating mantle which was controlled with a eurotherm controller connected to the thermocouple. The nitrogen sparge pipe was inserted so that the nitrogen flow agitated the flask contents and provided mixing during the course of the reaction. The nitrogen flow also served to entrain out the liberated methanol and force the reaction to completion.

To the flask was added dimethyl maleate (914.3 g). 2,7-octadienol (2375 g) and stannous oxalate (31.2 g). The mixture was sparged with nitrogen for 10 minutes to remove air and the nitrogen flow was then reduced to a level which ensured efficient mixing. The mixture was then heated in stages to 130° C. ( e.g. 80° C. for 10 minutes, then 100° C. for 10 minutes and then 180° C. for 10 minutes). The progress of the reaction was monitored by collection of the methanol collected in the Dean and Stark apparatus. In order to drive the reaction to completion the temperature was raised to 140° C. after 7 hrs at 130° C. When 90% of the methanol had been collected, the reaction mixture was sampled hourly and analysed by GC.

The reaction was adjudged complete when the level of the "half ester" (methyl octadienyl maleate/fumarate) fell to below 0.3% w/w and this took approximately 31 hours. At this point the heating was switched off and the reaction mixture allowed to cool to room temperature. The product from the reaction was then decanted from any solids in the reaction flask. This product was then charged to a heated, decanter (40° C.) with an equal volume of 5% w/w aqueous sodium hydroxide solution. The mixture was stirred for 20 minutes and then allowed to separate and the lower aqueous phase decanted. This base wash was repeated and the remaining organic phase was washed with saturated brine until the aqueous phase reached a steady pH. The organic phase was then heated (100° C.) under reduced pressure (<500 Pa (<5 mBar)) on a rotatory evaporator to remove residual water and the majority of the excess octadienol. After cooling, the product was filtered and transferred to a 5-liter three-necked round-bottomed quickfit flask t-his flask was equipped with a still-head condenser and receiver flask (Perkin triangle), a thermocouple, a stream inlet pipe, and a eurotherm controlled heating mantle. The apparatus was evacuated to 4000 Pa (40 mBar) and the product heated to 120° C. The supply of steam was then connected and the residual traces of octadienol were removed. The purification was judged complete when the volume of the heads product aqueous phase to increased more than times that of the organic phase. Alter cooling down the product was then treated with activated carbon (1% w/w, 100° C. 2 Hrs, <500 Pa (<5 mBar)) on a rotatory evaporator. The cooled mixture was filtered through dried celite to obtain the final product which had the following analyses:

| | |
|---|---|
| OH number | 4 mg KOH/g (titration) |
| total acid | 46 ppm KOH/g (titration) |
| maleic acid/anhydride | <10 ppm (HPLC) |
| Fumaric acid | <10 ppm (HPLC) |
| tin | <10 ppm (atomic absorption) |
| sodium | <20 ppm (atomic absorption, detection limit) |
| chlorine | <10 ppm (atomic absorption, detection limit) |
| GC "CPSil5" column | octadienyl methyl fumarate/maleate (0.11% w/w) |
| | di-(2,7-octadienyl) maleate (73% w/w) |
| | di-(2,7-octadienyl) fumarate (22% w/w) |
| | 2-(2,7-octadienoxy) di-(2,7-octadienyl) succinate (3% w/w) |

The GC assignment was supported by GC/MS and a $^1$H nmr and $^{13}$C nmr studies, The GC/MS used a VG Trio-1000, operated according to the manufacturers instructions under the following conditions:

GC column 25 m×0.32 mm DB5 (0.25 micron film)

temperature programme 40° C. (3 mins)@10C/min 320° C.(10 mins)

injection 1 microliter (1% solution in acetone) on column 40° C.

ammonia chemical ionisation (CI)

scan range 50–800 scan rate 1/s

It was found that the deductions of molecular weights from the Cl spectra is rather less straightforward than is usual on account of (a) extensive rearrangements of fumarates in particular giving [M+3] and [M+20] ions in addition to the usual [M+1] and [M+18] ions and (b) extensive fragmentation exhibited by some species. As a result the GC peaks were assigned by interpretation. In addition to the assigned peaks an additional species was identified which was assigned to a lactone. These assignments were confirmed by $^1$H and $^{13}$C nmr. Table 1 gives tentative assignments of the observed $^{13}$C nmr peaks. It should be noted that the two isomeric octadienols (2,7-octadienol and 1,7-octadien-3-ol) though not separable by the GC method used can be identified by nmr and are recorded in the nmr assignment Table 1. The correspondence to the GC was confirmed again by integration of the nmr spectrum of several samples in which the composition varied. The lactone found by GC/MS was also observed in the nmr and quantified at approximately 6.:2% (tentative structure given in Table 1).

TABLE 2

2,7-Octadienol;

$$\overset{8}{CH_2}=\overset{7}{CH}\cdot\overset{6}{CH_2}\cdot\overset{5}{CH_2}\cdot\overset{4}{CH_2}\cdot\overset{3}{CH}=\overset{2}{CH}\cdot\overset{1}{CH_2}\cdot OH$$

|       | 1  | 2     | 3     | 4    | 5    | 6  | 7     | 8     |
|-------|-----|-------|-------|------|------|----|-------|-------|
| Major | 63 | 132.8 | 129.5 | 31.3 | 28.6 | 33 | 138.5 | 114.5 |
| Minor | 58 | 132   | 129   | 26.6 | 28   | 33 | 135.5 | 114.5 |

Fumarate/Maleate $$\overset{8}{CH_2}=\overset{7}{CH}\,\overset{6}{CH_2}\cdot\overset{5}{CH_2}\,\overset{4}{CH_2}\,\overset{3}{CH}=\overset{2}{CH}\,\overset{1}{CH_2}\,O(=\overset{9}{O})C\,\overset{10}{C}=C\cdot C(=O)\cdot OR \quad (R = 2,7\text{-Octadienyl})$$

| Fumarate/Maleate | 1 | 2 | 3 | 4 | 5 | 6 | 7 | 8 | 9 | 10 |
|---|---|---|---|---|---|---|---|---|---|---|
| Maleate (major isomer) | 65.24 | 123.34 | 135.81 | 31.12 | 27.53 | 32.65 | 137.8 | 114.3 | 164.27 | 129.33 |
| Maleate (minor isomer)* | 60.4 | — | — | 26.39 | 28.04 | 32.65 | — | — | 164.42 | 129.39 |
| Fumarate (major isomer) | 65.35 | 123.31 | 136.16 | 31.2 | 27.58 | 32.73 | 137.81 | 114.42 | 163.96 | 133.12 |
| Fumarate (minor isomer)* | 68.72 | 122.83 | 135.02 | 26.49 | 28.1 | 32.79 | 137.81 | 114.51 | 164.07 | 133.21 |

2-(2,7-octadienoxy)di-2,7-octadienyl succinate:

$$\overset{8}{CH_2}=\overset{7}{CH}\,\overset{6}{CH_2}\,\overset{5}{CH_2}\,\overset{4}{CH_2}\,\overset{3}{CH}=\overset{2}{CH}\cdot\overset{1}{CH_2}\,O(O=)C\,\overset{9}{CH_2}\cdot\overset{10}{CH}\cdot(\overset{11}{C}(=O)\cdot O\cdot\overset{12}{CH_2}\cdot\overset{1'}{CH}=$$

$$\leftarrow 2'\;-\;8' \rightarrow \quad 1''\;2'' \quad 3''\;4''\;6\;\;5''\;7''\;8''$$
$$=CH\cdot CH_2\cdot CH_2\cdot CH_2\cdot CH=CH_2)\cdot O\cdot CH_2\cdot CH=CH\cdot CH_2\cdot CH_2\cdot CH_2\cdot CH=CH_2$$

NB Due to the loss of symmetry (of maleate of fumarate) in the molecule, all the octadienyl/octadienoxy groups are magnetically inequivalent.

|       | 1     | 2      | 3     | 4,4',4" | 5,5'  | 6,6',6" | 7,7'   | 8,8'   | 9      | 10    | 11    | 12     |
|-------|-------|--------|-------|---------|-------|---------|--------|--------|--------|-------|-------|--------|
| Major | 65.15 | 123.52 | 135.9 | 31.2    | 27.58 | 32.73   | 137.81 | 114.51 | 169.18 | 37.53 | 73.51 | 170.69 |
| Minor | 60.31 | —      | —     | 26.49   | 28.1  | 32.79   | —      | —      | 169.27 | —     | 73.7  | 170.78 |

|       | 1'    | 2'     | 3'     | 1''   | 2''    | 3''    | 5''   | 7''    | 8''   |
|-------|-------|--------|--------|-------|--------|--------|-------|--------|-------|
| Major | 64.94 | 123.75 | 135.38 | 71.24 | 125.66 | 134.55 | 27.76 | 137.96 | 114.2 |
| Minor | 60.13 | —      | —      | 65.89 | —      | —      | —     | —      | —     |

Lactones: Species believed to be lactones have been identified in the octadienyl ester samples. Whilst there appear to be two possible isomers of this lactone, the $^{13}$C NMR data fits the structure:

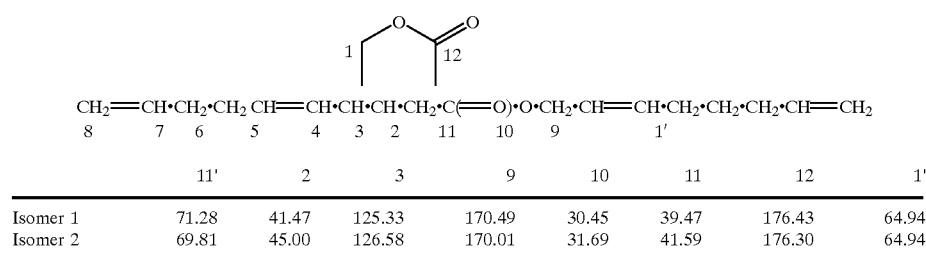

| | 11' | 2 | 3 | 9 | 10 | 11 | 12 | 1' |
|---|---|---|---|---|---|---|---|---|
| Isomer 1 | 71.28 | 41.47 | 125.33 | 170.49 | 30.45 | 39.47 | 176.43 | 64.94 |
| Isomer 2 | 69.81 | 45.00 | 126.58 | 170.01 | 31.69 | 41.59 | 176.30 | 64.94 |

The mixed ester product from step (a) comprising a relatively low amount the 2-succinate ester is reacted in a step (b) with a second reactant alcohol in the presence of a magnesium alkoxide catalyst as follows:

Step (b): Allyloxysuccinate Enhancement—General method

All apparatus used was dried ( 10° C. oven) before use and the liquid agents were be dried ( <0.05% w/w water—molecular sieves 3a). The total acid number (TAN) of the ester reagent was measured.

To a conical flask was charged a pear shaped magnetic follower:

| | |
|---|---|
| The mixed ester product from step (a) | 546.6 g |
| 2,7-Octadienol | 414.82 g |
| magnesium ethoxide # | 4.858 g |

[assuming that 1 mole of acid is neutralised by 1 mole of magnesium ethoxide,

| | | |
|---|---|---|
| 1 ppm KOH/g is = | 1 × 10⁻⁶/Mol Wt of KOH | moles KOH/g |
| | 1 × 10⁻⁶/56.11 | moles KOH/g |

The molecular weight of magnesium ethoxide =114.44

So TAN of 1 ppm KOH will require $114.44 \times 1 \times 10^{-6}/56.11$ g

If the sample weighs Y grams, if the sample TAN is Z ppm/KOH then the amount of magnesium ethoxide required to neutralise the acid in the sample=$114.44 \times Y \times Z \times 10^{-6}/56.11$.

To this amount must be added the amount of magnesium ethoxide needed to catalyse the reaction eg 035% w/w.]

A nitrogen top cover was supplied to the flask and the mixture with magnetic stirring heated to 80° C. The reaction was monitored by GC and samples withdrawn at different degrees of conversion.

The samples were purified by using the following procedure.

An equal volume of saturated brine was added to the sample in the separating funnel and the mixture shaken for 5 minutes. The mixture separated into two phases, an upper organic phase and a lower aqueous phase. The lower aqueous phase was decanted and the procedure repeated until the the aqueous layer pH deceased to 7±0.5. To the upper organic phase was added 1% w/w activated carbon and the mixture was heated to 100° C. for the at 133.3 Pa (1 mmHg) on a rotatory evaporator. The material was then allowed to cool to room temperature and filtered through a cake of dried celite filter aid. It was found that was possible to obtain conversions of the maleate starting material to the allyloxysuccinate ill excess of 97% by this method.

2. Testing of reactive diluents in paint formulations:

A good reactive diluent must meet a range of criteria including low odour and toxicity, low viscosity and the ability to "cut" the viscosity of the paint to facilitate application on the surface to be coated therewith. Furthermore, the diluent should not have a markedly adverse effect on the properties of the paint film such as drying speed, hardness, degree of wrinkling, durability and tendency to yellowing. The reactive diluents described above have therefore been tested in paint applications using both clear and pigmented paints. The diluents have been compared with paints formulated using white spirit, a conventional thinner.

2.1 Unpigmented "Clearcoat" Formulations:

2.1.1 Materials Used

Unpigmented ("clearcoat") paint formulations were prepared using a high solids alkyd resin SETAL®EPL 91/1/14 (ex AKZO NOBEL, and described in "Polymers Paint and Colour Journal, 1992, 182, pp. 372). In addition to the diluent. Siccatol®938 drier (ex AKZO NOBEL) and methyl ethyl ketone-oxime (hereafter "MEK-oxime") anti-skinning agent were used. Where used, the white spirit was Exxon type 100. The nominal proportions of the above materials in the paint formulators were:

TABLE 2

| Materials | Parts by weight |
|---|---|
| Resin + Diluent | 100.0 |
| Siccatol 938 | 6.7 |
| MEK-oxime | 0.5 |

Note that, for white spirit formulations only, the proportions of drier and antiskinning agent were calculated on the basis of the resin only. Thus, the concentration of these components in the paint was lower than for other diluents.

2.1.2 Method of Preparation of Clearcoat Formulations:

Alkyd resin and diluent (2-(2.7-octadienoxy)-di-2,7-octadienyl succinate) were mixed in glass jars for 2 hours (eg using a Luckhain multi-mix roller bed) in the proportions required to achieve a viscosity (measured via the ICI cone and plate method using a viscometer supplied by Research Equipment (London) Limited) of 68±3 Pax (6.8±0.3 poise). Typically, this resulted it, a mixture which was ca. 85% w/w resin. If further additions of diluent or resin were required to adjust the viscosity to 68±3 Pa s (6.8 ±0.3 poise). a further hour of mixing was allowed. The required quantity of drier was added and, after mixing (1 hour). the required amount of anti-skinning agent was added, after final mixing for at least 30 minutes, the viscosity of the mixture was measured to ensure that the viscosity was between 61 and 69 Pa s (6.1 and 6.9 poise).

The mixture ("formulation") was then divided into two jars so as to leave ca. 10–15% v/v headspace of air in the sealed jars. One of the jars was stored at 23° C. in darkness for 7 days before paint applications tests were performed. The second jar was stored ("aged") at 35° C. in daylight for 14 days before applications tests were performed.

3. Test Procedures used for Clearcoat Formulations:

3.1 Application of paint films:

Thin films were applied to cleaned glass test plates using Sheen cube or draw-bar applicators with a nominal 75 µm gap widths 3.2 Viscosity measurements and results:

The viscosity of each diluent was measured at 23° C. using a suspended level viscometer. Densities of the diluents were taken as an average of three readings made at 25° C. using density bottles with a nominal 10 cm³ capacity, calibrated with water.

TABLE 3

Viscosity of reactive diluents

| Diluent | Viscosity (m Pa.s) |
|---|---|
| AK2R (Example S3) | 18 |

3.3 Drying Performance:

Drying performance was measured using films applied to 30 cm×2.5 cm glass strips and BK drying recorders. The BK recorders were enclosed in a Fisons controlled temperature and humidity cabinet so that the drying experiment could be performed at 10° C. and at 70% relative humidity. Sample performance was assessed on the basis of the second stage of drying (dust drying time, T2)

TABLE 4

SAMPLES PREPARED BY THE ABOVE PROCESS USING MAGNESIUM ETHOXIDE & TEST DATA

| | Solvent Description | Fresh Drying Times (hrs) | Aged Drying Times (hrs) |
|---|---|---|---|
| Solvent-1 | Di-octadienyl maleate prepared with 0.1% MSA and treated with magnesium ethoxide (7% succinate, reaction interrupted) | 11.88 9.26 | 13.86 13.09 |
| | Solvent-1 treated further with magnesium ethoxide (58% succinate) | 7.6 | 9.53 |
| Solvent-2 | Dioctadienyl maleate prepared with 0.1% dibutyl tin oxide | 10.47 | 13.56 |
| | Solvent-2 treated with magnesium ethoxide (75% + succinate) | 6.83 | 9.7 |

The above process was repeated with the product from Example 1 using the enhancement method (b) which achieved an allyloxy succinate yield of 97%. The corresponding drying times were as follows:.

| Fresh | Aged |
|---|---|
| 5.6 hours | 5.4 hours |

What is claimed is:

1. A process for producing 2-substituted succinate esters of the formula (1) and process comprising reacting
   a. a dicarboxylic compound selected from the group consisting of maleic acid, maleic anhydride, fumaric acid and the dialkyl ester of maleic or fumaric acid with an alcohol $R^1O[CHR^{11}CH_2O]_xH$ where x is 0 or an integer from 1–6 in the presence of an esterification catalyst to form a hydrocarbyl ester or, when x=1–6, a hydrocarbyloxy alkylene ester of maleic and/or fumaric acid and
   b. the hydrocarbyl or hydrocarbyloxy alkylene ester from step (a) with an alkaline earth metal alkoxide in the presence of a further amount of the alcohol to form the 2-substituted succinate ester of formula (I)

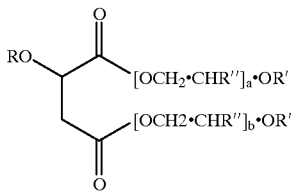

(I)

in which
   $R^1$=R and is an unsaturated hydrocarbyl or allyically unsaturated is hydrocarbyloxy allylene group having at least 5 carbon atoms, $R^{11}$ is H or an alkyl or an alkylene group having 1 to 2 carbon atoms and, each of a and b is same or different and has a value of 0 or is an integer from 1–6.

2. A process according to claim 1 wherein $R^1$ is derived from the reactant alcohol $R^1O[CHR^{11}CH_2O]_xH$ where x is 0 or an integer from 1–6 which is used for making the succinate ester.

3. A process according to claim 1 wherein the reactant alcohol is an allylic alcohol selected from the group consisting of 2-ethyl-hex-2-en-1-ol; 2-octen-1-ol; 1-octen-3-ol; 2,7-octadienol; 2-ethyl allyl alcohol; hept-3-en-2ol; 4-methyl pent-3-en-2-ol; 4-t-butoxy but-2-en-1-ol; 4-n-butoxy but-2-en-1-ol; cinnamyl alcohol; and isophorol.

4. A process according to claim 1 wherein the esterification catalyst used is selected from zinc acetate, dibutyl tin oxide, stannous oxalate, para-toluene sulphonic acid and phosphoric acid.

5. A process according to claim 1 wherein the reaction for making succinate esters of formula (I) is carried out at a temperature below 120° C.

6. A process according to claim 1 wherein the ester product from this step (a) is then further reacted in a step (b) with a further amount of the reactant alcohol in the presence of an alkaline earth metal alkoxide catalyst at a temperature below 120° C. and at a pressure in the range from atmospheric to 50 Kpa to enhance the amount of the desired 2-succinate ester in the product from step (a) at the expense of the maleates and fumarates in said product.

7. A process according to claim 6 wherein the alkaline earth metal alkoxide is magnesium alkoxide.

8. A process according to claim 7 wherein reaction of 2-ethyl hexenol with maleic acid or anhydride followed by reaction of the product with magnesium alkoxide of 2-ethylhexenol as catalyst gives rise to a product which primarily comprises 2- (2-ethyl hexenoxy) -di [2- (2-ethyl hexenyl)] succinate.

9. A process according to claim 3 wherein reaction of octadienoxy ethanol with maleic acid or anhydride followed by the reaction of the product with the magnesium alkoxide of octadienoxy ethanol as catalyst gives rise to a product comprising di-2-(octadienoxy)ethyl)-2-(2-octadienoxy) ethoxy) succinate.

10. A paint or coating formulation based on alkyd resins and comprising 2-octadienoxy di-octadienyl succinate as a reactive diluent in a paint or coating.

11. A paint or coating formulation based on alkyd resins according to claim 10 wherein said formulation also contains one or more of butylated hydroxy-toluene (2,6-butoxy-4-methyl phenol) and 2,4,6-tert-butyl phenol to inhibit haze and/or peroxidation.

12. 2-octadienoxy di-octadienyl succinate.

* * * * *